(12) United States Patent
Akagane (10) Patent No.: US 11,504,180 B2
(45) Date of Patent: Nov. 22, 2022

(54) MEDICAL DEVICE

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 638 days.

(21) Appl. No.: 16/407,233

(22) Filed: May 9, 2019

(65) Prior Publication Data

US 2019/0262062 A1    Aug. 29, 2019

Related U.S. Application Data

(63) Continuation of application No. PCT/JP2016/083227, filed on Nov. 9, 2016.

(51) Int. Cl.
*A61B 18/14* (2006.01)
*A61B 18/08* (2006.01)
(Continued)

(52) U.S. Cl.
CPC .......... *A61B 18/1442* (2013.01); *A61B 18/08* (2013.01); *A61B 18/085* (2013.01);
(Continued)

(58) Field of Classification Search
CPC .......... A61B 18/085; A61B 2018/1412; A61B 2018/00589; A61B 2018/1452;
(Continued)

(56) References Cited

U.S. PATENT DOCUMENTS 3,970,088 A * 7/1976 Morrison ........... A61B 18/1402
606/48
5,308,311 A * 5/1994 Eggers ................ A61B 18/082
606/29
(Continued)

FOREIGN PATENT DOCUMENTS

JP    2001-198137 A    7/2001
JP    2001355960 A  * 12/2001
(Continued)

OTHER PUBLICATIONS

English Translation of WO-2015122351-A1, Global Dossier (Year: 2015).*
(Continued)

*Primary Examiner* — Ronald Hupczey, Jr.
*Assistant Examiner* — Marina Delaney Templeton
(74) *Attorney, Agent, or Firm* — Oliff PLC (57) ABSTRACT

A medical device includes a thermal source that generates heat, a base that has an outer surface and to which the heat from the thermal source is transferred, a first coating that contacts one part of the outer surface of the base and a second coating that is provided on the outer surface of the base, and is exposed and electrically conductive. The second coating supplies, a high-frequency current to an object to be treated. The medical device also includes a laminated portion that includes the first coating in the outer surface of the base extends and a portion of the second coating that is laminated on the first coating.

13 Claims, 6 Drawing Sheets

(51) Int. Cl.
*A61B 17/295* (2006.01)
*A61B 18/00* (2006.01)

(52) U.S. Cl.
CPC .......... *A61B 18/14* (2013.01); *A61B 18/1445* (2013.01); *A61B 17/295* (2013.01); *A61B 18/1402* (2013.01); *A61B 2018/00071* (2013.01); *A61B 2018/00077* (2013.01); *A61B 2018/00101* (2013.01); *A61B 2018/00107* (2013.01); *A61B 2018/00589* (2013.01); *A61B 2018/00994* (2013.01); *A61B 2018/1412* (2013.01); *A61B 2018/1452* (2013.01)

(58) Field of Classification Search
CPC .......... A61B 17/295; A61B 2018/0071; A61B 2018/00089; A61B 18/08; A61B 2018/00107; A61B 2018/00148; A61B 2018/00077; A61B 2018/00083; A61B 2018/00095; A61B 2018/00101; A61B 18/14

See application file for complete search history.

(56) References Cited

U.S. PATENT DOCUMENTS

| | | | | |
|---|---|---|---|---|
| 5,976,132 | A * | 11/1999 | Morris | A61B 18/1445 606/49 |
| 6,296,637 | B1 * | 10/2001 | Thorne | A61B 18/1402 606/41 |
| 8,500,735 | B2 * | 8/2013 | Tanaka | A61B 18/1442 606/51 |
| 8,647,343 | B2 * | 2/2014 | Chojin | A61B 18/1445 606/51 |
| 9,439,711 | B2 * | 9/2016 | Keller | A61B 18/1445 |
| 2003/0060816 | A1 * | 3/2003 | Iida | A61B 18/085 606/29 |
| 2003/0078577 | A1 * | 4/2003 | Truckai | A61B 18/1442 606/51 |
| 2003/0171747 | A1 * | 9/2003 | Kanehira | A61B 18/085 606/45 |
| 2003/0187429 | A1 * | 10/2003 | Karasawa | A61B 18/085 606/28 |
| 2005/0021017 | A1 | 1/2005 | Karasawa et al. | |
| 2005/0288747 | A1 * | 12/2005 | Aoki | A61B 18/085 607/96 |
| 2009/0048589 | A1 * | 2/2009 | Takashino | A61B 18/1445 606/28 |
| 2014/0228844 | A1 * | 8/2014 | Horlle | A61B 18/085 606/49 |
| 2015/0080887 | A1 * | 3/2015 | Sobajima | A61B 18/085 606/41 |
| 2018/0250066 | A1 * | 9/2018 | Ding | A61B 18/1442 |

FOREIGN PATENT DOCUMENTS

| | | | | |
|---|---|---|---|---|
| JP | 2004-188012 | A | 7/2004 | |
| JP | 2014-529452 | A | 11/2014 | |
| WO | 2013/180293 | A1 | 12/2013 | |
| WO | 2013/180294 | A1 | 12/2013 | |
| WO | WO-2014119137 | A1 * | 8/2014 | .......... A61B 18/085 |
| WO | WO-2014141530 | A1 * | 9/2014 | ........ A61B 18/1445 |
| WO | WO-2015122351 | A1 * | 8/2015 | .......... A61B 18/085 |
| WO | 2016/080147 | A1 | 5/2016 | |

OTHER PUBLICATIONS

English Translation of WO-2014141530-A1, Global Dossier (Year: 2014).*

English Translation of WO-2014119137-A1, Global Dossier (Year: 2014).*

English Translation of JP-2001355960-A, Global Dossier (Year: 2001).*

Feb. 4, 2021 Office Action issued in Chinese Patent Application No. 201680090703.5.

May 14, 2019 Translation of International Preliminary Report on Patentability issued in International Patent Application No. PCT/JP2016/083227.

Jan. 31, 2017 International Search Report issued in International Patent Application No. PCT/JP2016/083227.

* cited by examiner

MEDICAL DEVICE

CROSS-REFERENCE TO RELATED APPLICATIONS

This is a Continuation Application of PCT Application No. PCT/JP2016/083227, filed Nov. 9, 2016, the entire contents of which are incorporated herein by reference.

BACKGROUND

Exemplary embodiments relate to a medical device for treating an object to be treated using heat and high-frequency current.

Medical devices can treat a living tissue gripped between a pair of gripping pieces. In the medical devices, high-frequency current and heat generated by a thermal source are applied to the object to be treated gripped between the pair of gripping pieces. The object to be treated is coagulated by high-frequency current and incised by heat generated by the thermal source.

For treatments in which an object to be treated is to be incised and coagulated using a medical device, it is desired that the heat generated by the thermal source not be transmitted to living tissue or the like other than the object to be treated. Thus, there is a desire for heat generated by the thermal source to the outside of the gripping region between the pair of gripping pieces to be reduced.

SUMMARY

Exemplary embodiments provide a medical device that reduces heat generated by the thermal source in locations other than the object to be treated.

A medical device can include a thermal source that generates heat, a base that has an outer surface that receives the heat, a first coating that contacts one part of the outer surface of the base, and a second coating that is provided on the outer surface of the base. The second coating can be exposed and can be electrically conductive, and can also supply a high-frequency current to an object to be treated. The medical device can also include a laminated portion that includes the part of the that extends along the outer surface of the base and part of the second coating that is laminated on the first coating.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Figure 1:
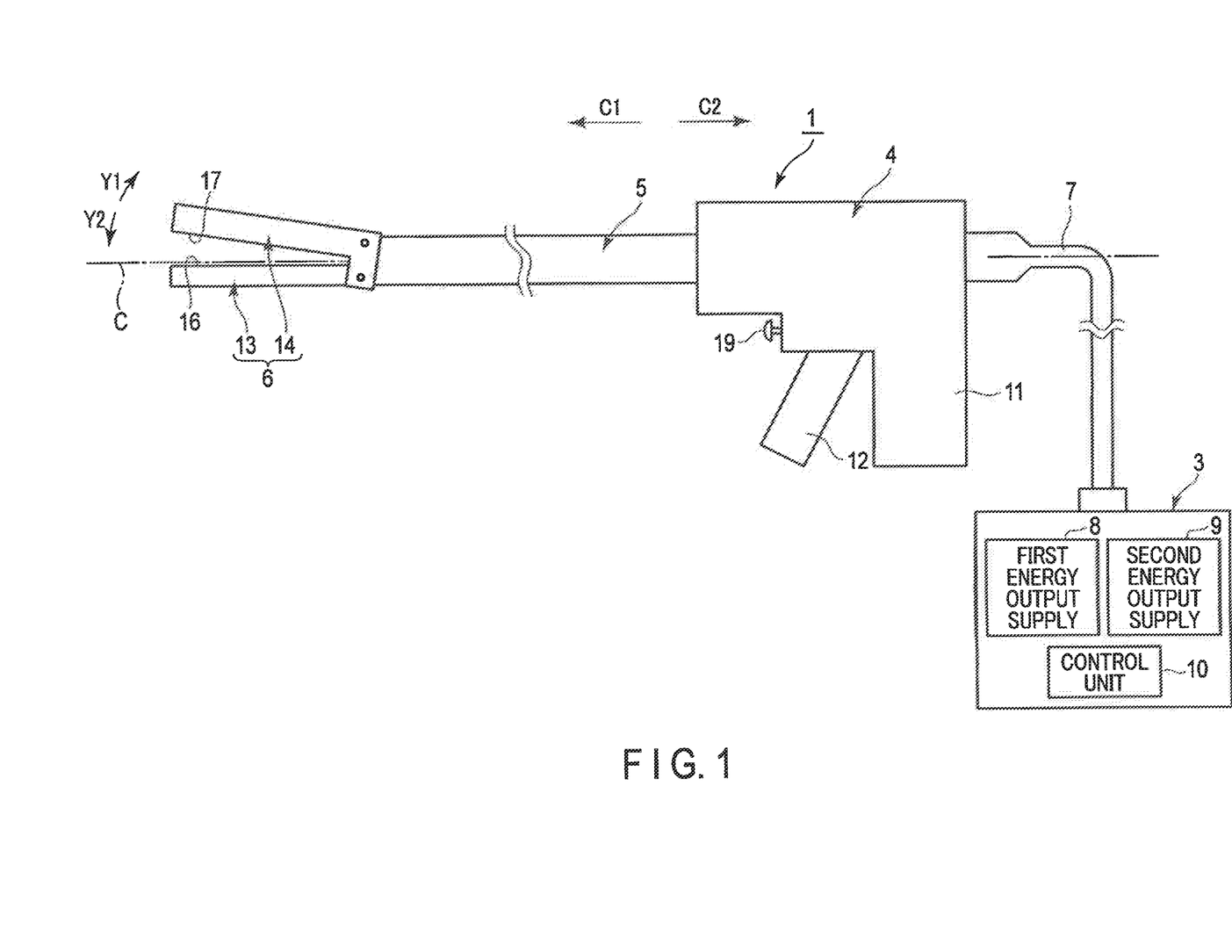
FIG. 1 is a schematic view showing a treatment system that uses an energy treatment instrument according to an exemplary embodiment.

FIG. 1 is a view showing a treatment system in which an energy treatment instrument 1 being a medical device is used. As shown in FIG. 1, the energy treatment instrument 1 has a longitudinal axis C. Here, in the energy treatment instrument 1, the direction along the longitudinal axis C will be referred to as the longitudinal direction. Also, one side in the longitudinal direction will be referred to as the distal side (arrow C1 side), while the side opposing the distal side will be referred to as the proximal side (arrow C2 side). In the present embodiment, the energy treatment instrument 1 is a thermal treatment tool for treating a gripped object to be treated by using heat, includes two treatment electrodes, and is a bipolar high-frequency treatment tool that treats the gripped object to be treated by using high-frequency current (high-frequency energy) flowing between these electrodes.

The energy treatment instrument 1 is provided with a housing 4 capable of holding, a shaft 5 connected to the distal side of the housing 4, and an end effector 6 provided at a distal portion of the shaft 5. One end of a cable 7 is connected to the housing 4. The other end of the cable 7 is separably connected to a power supply unit 3. The power supply unit 3 is provided with a first energy output supply 8, a second energy output supply 9, and a control unit 10. The first energy output supply 8 is provided with a conversion circuit or the like for converting electric power from a battery power supply or an outlet power supply into electric energy (direct current electric power or alternating electric power) to be supplied to the thermal source to be described later, and outputs the converted electric energy. The second energy output supply 9 is provided with a conversion circuit or the like for converting electric power from the battery power supply or the outlet power supply into electric energy (high frequency electric power) to be supplied to the electrodes to be described later, and outputs the converted electric energy. The control unit 10 is provided with an integrated circuit or processor that includes a CPU (Central Processing Unit), an ASIC (Application Specific Integrated Circuit), an FPGA (Field Programmable Gate Array) or the like, and a storage medium.

Attached to the housing 4 is an operation button 19 as an energy operation input unit. By pressing the operation button 19, the power supply unit 3 is operated (a signal is input to the power supply unit 3) to output electric energy from the first energy output supply 8 and/or the second energy output supply 9 to the energy treatment instrument 1. It should be noted that instead of or in addition to the operation button 19, a foot switch or the like separate from the energy treatment instrument 1 may be provided as the energy operation input unit.

Provided in the housing 4 is a grip (fixed handle) 11, and a handle (movable handle) 12 is rotatably attached. As the handle 12 rotates relative to the housing 4, the handle 12 opens or closes with respect to the grip 11. It should be noted that in the present embodiment, the handle 12 is located on the distal side with respect to the grip 11 and moves, during an opening or closing operation, substantially in parallel to the longitudinal axis C with respect to the grip 11. However, the invention is not limited thereto. For example, in one embodiment, the handle 12 may be located proximally with respect to the grip 11. In another embodiment, the handle 12 may be located on the side opposing the grip 11 with respect to the longitudinal axis C, and the movement direction during the opening or closing movement with respect to the grip 11 may intersect the longitudinal axis C (may be substantially perpendicular).

Figure 2:
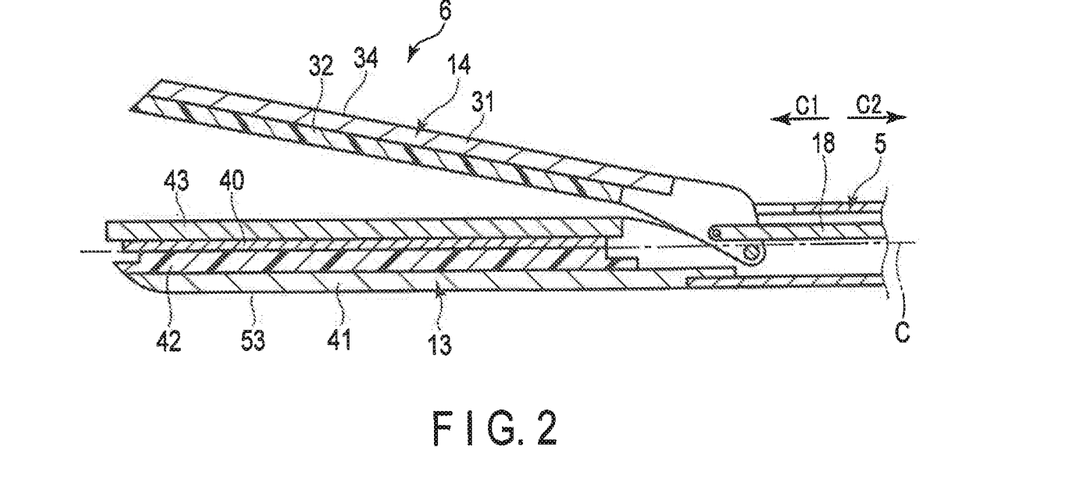
FIG. 2 is a cross-sectional view schematically showing an end effector according to an exemplary embodiment in a cross section substantially perpendicular to a width direction.

FIG. 2 is a view showing the shaft 5 and the end effector 6. As shown in FIGS. 1 and 2, the shaft 5 extends along the longitudinal axis C. Further, the end effector 6 is provided with a first gripping piece 13 and a second gripping piece 14 (jaw) that opens and closes between the first gripping piece 13. The first gripping piece 13 is provided with a first opposing surface 16 opposing the second gripping piece 14. Further, the second gripping piece 14 is provided with a second opposing surface 17 opposing the first gripping piece 13 and the first opposing surface 16. The space between the handle 12 and the second gripping piece 14 is connected via a movable member 18 extending along the longitudinal axis C to the interior of the shaft 5. By opening or closing, with respect to the grip 11, the handle 12 being an opening/closing operation input unit, the movable member 18 moves along the longitudinal axis C with respect to the shaft 5 and the housing 4, and the pair of gripping pieces 13, 14 opens or closes. By closing the gripping pieces 13, 14, living tissues such as blood vessels can be gripped as the object to be treated between the first gripping piece 13 and the second gripping piece 14. When the gripping pieces 13, 14 are closed, the gripping pieces 13, 14 extend along the longitudinal direction. In the present embodiment, the first gripping piece 13 is fixed to the shaft 5, and the second gripping piece 14 is rotatably attached to the distal portion of the shaft 5.

The opening/closing directions of the end effector 6 intersect (become substantially perpendicular to) the longitudinal axis C. Of the opening/closing directions of the end effector 6, the direction in which the second gripping piece 14 opens with respect to the first gripping piece 13 will be referred to as the opening direction of the second gripping piece 14 (arrow Y1 side in FIG. 1), while the direction in which the second gripping piece 14 closes with respect to the first gripping piece 13 will be referred to as the closing direction of the second gripping piece 14 (arrow Y2 side in FIG. 1). Further, the direction intersecting the longitudinal axis C and the opening/closing direction of the second gripping piece 14 will be referred to as the width direction of the end effector 6.

It should be noted that the first gripping piece 13 and the second gripping piece 14 may be provided at the distal portion of the shaft 5 and that the gripping piece 14 may be configured to open/close. For example, in one embodiment, the first gripping piece 13 is formed integrally with the shaft 5. The second gripping piece 14 is rotatably attached to the distal portion of the shaft 5. In another embodiment, both the first gripping piece 13 and the second gripping piece 14 are rotatably attached to the distal end of the shaft 5.

Figure 3:
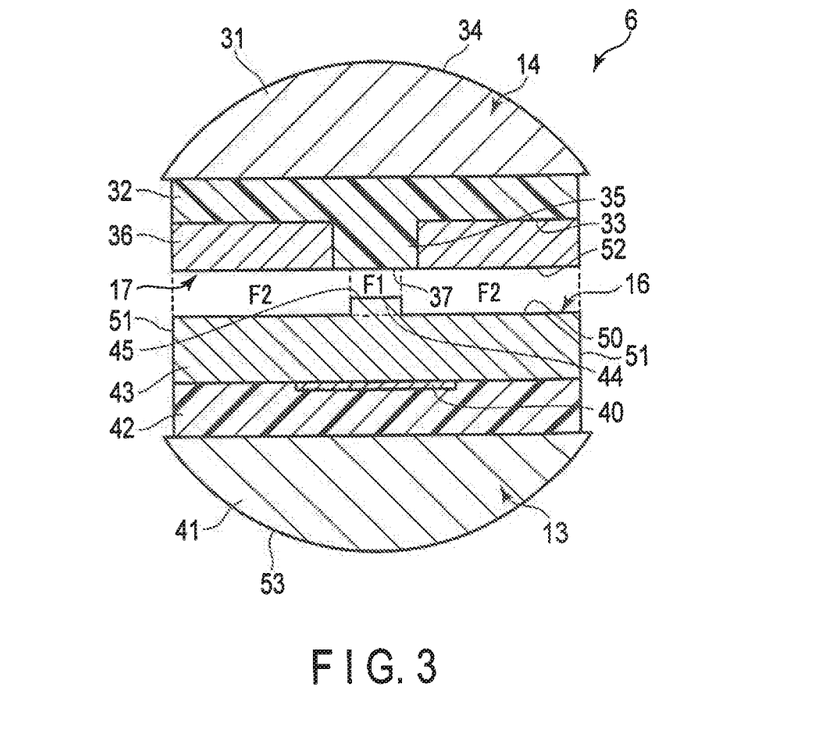
FIG. 3 is a cross-sectional view schematically showing the end effector according to an exemplary embodiment in a cross section substantially perpendicular to a longitudinal axis.

FIG. 3 is a view showing the first gripping piece 13 and the second gripping piece 14 in a cross section substantially perpendicular to the longitudinal axis C. As shown in FIGS. 2 and 3, the first gripping piece 13 is provided with a supporting member 41. The supporting member 41 is formed from, for example, a metal such as stainless steel. The supporting member 41 extends from the proximal portion of the first gripping piece 13 to the distal portion along the direction of extension of the first gripping piece 13. In the first gripping piece 13, a back surface 53 facing the side opposing the first opposing surface 16 is formed by the supporting member 41. In the first gripping piece 13, the back surface 53 is exposed to the outside.

Fixed to the supporting member 41 on the side of the second gripping piece 14 is a heat-insulating member 42. The heat-insulating member 42 extends from the proximal portion of the first gripping piece 13 to the distal portion along the direction of extension of the first gripping piece 13. The heat-insulating member 42 is formed from a highly heat-insulating, electrically non-conductive material.

Fixed to the side of the second gripping piece 14 of the heat-insulating member 42 is a thermally transmitting member 43 (base). The thermally transmitting member 43 is highly thermally transmitting and electrically conductive. The thermally transmitting member 43 is formed from, for example, a metal or the like. The thermally transmitting member 43 is electrically connected to the second energy output supply 9 of the power supply unit 3 via an electric path (not shown) that extends through the inside of the first gripping piece 13, the inside of the shaft 5, the inside of the housing 4, and the inside of the cable 7. By supplying electric energy (high frequency electric power) from the second energy output supply 9, the thermally transmitting member 43 functions as a (first) electrode. The heat-insulating member 42 is electrically non-conductive. Therefore, electric energy from the second energy output supply 9 is supplied (transmitted) neither to the supporting member 41 nor the heat-insulating member 42.

The thermally transmitting member 43 is provided with a lateral surface 51 facing the width direction of the first gripping piece 13, a planar surface portion 50 facing the side of the second gripping piece 14, and a protruding portion 44 protruding from the planar surface portion 50 towards the side of the second gripping piece 14. The protruding portion 44 is provided with a protruding surface 45 facing the side of the second gripping piece 14. In the opening/closing direction of the end effector 6, the protruding surface 45 is located further to the side of the second gripping piece 14 than to the side of the planar portion 50. In the first gripping piece 13, the first opposing surface 16 is formed by the planar surface portion 50 and the protruding portion 44.

Provided between the heat-insulating member 42 and the thermally transmitting member 43 is a thermal source 40. The thermal source 40 is fixed to the heat-insulating member 42 from the side of the first opposing surface 16. The thermal source may be a heater. Further, the thermal source 40 is fixed to the thermally transmitting member 43 from the side of the back surface 53. The thermal source 40 is electrically connected to the first energy output supply 8 of the power supply unit 3 via the electric path (not shown) extending through the inside of the first gripping piece 13, the inside of the shaft 5, the inside of the housing 4, and the inside of the cable 7. When electric energy (DC power or AC power) is supplied from the power supply unit 3 to the thermal source 40 via the electric path, heat is generated in the thermal source 40. Heat generated by the thermal source 40 is transmitted through the thermally transmitting member 43 to the planar surface portion 50 and the protruding portion 44. It should be noted that the heat-insulating member 42 is highly heat-insulating. For this reason, the heat generated by the thermal source 40 is hardly transmitted to the supporting member 41 and the heat-insulating member 42.

The second gripping piece 14 is provided with a supporting member 31. The supporting member 31 is formed from, for example, a metal such as stainless steel. The supporting member 31 extends from the proximal portion to the distal portion of the second gripping piece 14 along the direction of extension of the second gripping piece 14. The proximal portion of the supporting member 31 is connected to the shaft 5 and the movable member 18. In the second gripping piece 14, a back surface 34 facing the side opposing the second opposing surface 17 is formed by the supporting member 31. In the second gripping piece 14, the back surface 34 is exposed to the outside.

Fixed to the supporting member 31 on the side of the first gripping piece 13 is a heat-insulating member 32. The heat-insulating member 32 extends from the proximal portion of the second gripping piece 14 to the distal portion along the direction of extension of the second gripping piece 14. The heat-insulating member 32 is formed from a highly heat-insulating, electrically non-conductive material. The heat-insulating member 32 is provided with a base surface 33 facing the side of the first gripping piece 13, and a protruding portion 35 protruding from the base surface 33 to the side of the first gripping piece 13. The protruding portion 35 extends from the proximal portion of the second gripping piece 14 to the distal portion along the direction of extension of the second gripping piece 14. Formed in the protruding portion 35 is an abutting surface 37 facing the side of the first gripping piece 13.

Fixed on the base surface 33 is an electrically conductive member 36. The electrically conductive member 36 is fixed to the base surface 33 from the side of the first gripping piece 13. The electrically conductive member 36 extends from the proximal portion of the second gripping piece 14 to the distal portion along the direction of extension of the second gripping piece 14. The electrically conductive member 36 is formed in a ring shape surrounding the protruding portion 35 in the width direction and the direction of extension of the second gripping piece 14. The electrically conductive member 36 is formed from an electrically conductive material. The electrically conductive member 36 is provided with an electrode surface 52 facing the side of the first gripping piece 13. In the second gripping piece 14, the second opposing surface 17 is formed by the electrode surface 52 and the abutting surface 37.

The electrically conductive member 36 is electrically connected to the second energy output supply 9 of the power supply unit 3 via an electric path (not shown) extending through the inside of the second gripping piece 14, the inside of the shaft 5, the inside of the housing 4, and the inside of the cable 7. By supplying electric energy (high frequency electric power) from the second energy output supply 9, the electrically conductive member 36 functions as a (second) electrode, in other words, different from the thermally transmitting member 43 (first electrode). The heat-insulating member 32 is formed from an electrically non-conductive material. For this reason, the electric energy from the second energy output supply 9 is supplied (transmitted) neither to the supporting member 31 nor the heat-insulating member 32.

When the first gripping piece 13 and the second gripping piece 14 are closed but there is no object to be treated between the first gripping piece 13 and the second gripping piece 14, the abutting face 37 abuts the protruding surface 45. In that case, the planar surface portion 50 and the electrode surface 52 are not in contact. In other words, the thermally transmitting member 43 and the electrically conductive member 36 are not in contact. This prevents short circuits caused by contact between the thermally transmitting member 43 and the electrically conductive member 36.

Formed between the first opposing surface 16 and the second opposing surface 17 is a gripping region in which the object to be treated is to be gripped. In this gripping region, the region formed between the abutting surface 37 and the protruding surface 45 will be referred to as a first gripping region F1, and the region formed between the electrode surface 52 and the planar surface portion 50 will be referred to as a second gripping region F2. The second gripping region F2 is formed on both sides of the first gripping region F1 in the width direction of the end effector 6. In the second gripping region F2, the planar surface portion 50 opposes the electrode surface 52 that is formed by the second electrode (electrically conductive member 36). The distance between the first opposing surface 16 and the second opposing surface 17 in the first gripping region F1 is smaller than the distance between the first opposing surface 16 and the second opposing surface 17 in the second gripping region F2. When the gripping pieces 13, 14 are closed, the abutting surface 37 is pressed by the protruding surface 45 to the side of the second gripping piece 14. Therefore, the force with which the first gripping piece 13 presses the second gripping piece 14 in the first gripping region F1 is larger than the force with which the first gripping piece 13 presses the second gripping piece 14 in the second gripping region F2. In other words, the first opposing surface 16 is provided with a first portion (45) forming the first gripping region F1, and a second portion (50) that forms the second gripping region F2 and presses the second gripping piece 14 with less force than the first portion.

Figure 4:
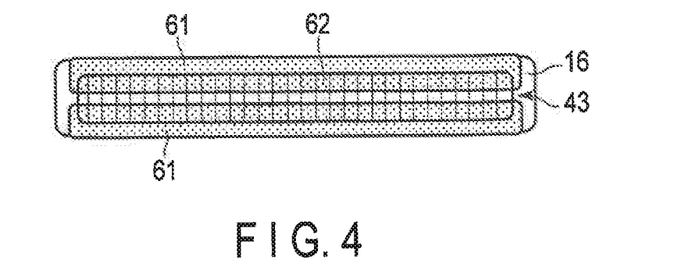
FIG. 4 is a schematic view showing a thermally transmitting member according to an exemplary embodiment as viewed from a second gripping piece side.

FIG. 4 is a view showing the first opposed surface 16 of the first gripping piece 13 as seen from the side of the second gripping piece 14. As shown in FIG. 4, coated on one part of the outer surface of the thermally transmitting member 43 along the longitudinal direction is a heat-insulating coating 61 (first coating) that is a thin film. In FIG. 4, the heat-insulating coating 61 is indicated by the dotted hatching. Further, coated on one part of the outer surface of the thermally transmitting member 43 along the longitudinal direction is an electrically conductive coating 62 (second coating) that is a thin film. In FIG. 4, the electrically conductive coating 62 is indicated by the hatching with the vertical lines. On the outer surface of the thermally transmitting member 43, the electrically conductive coating 62 is exposed to the outside.

The heat-insulating coating 61 is formed from an electrically non-conductive material less thermally transmitting than the thermally transmitting member 43. In one embodiment, the heat-insulating coating 61 is formed from a resin material that is a heat-resistant resin (such as PEEK, LCP, polyimide, polyamide, fluororesin). In another embodiment, the heat-insulating coating 61 is formed from a resin material and has an irregular surface. In that case, the heat-insulating coating 61 has less contact area with the surrounding tissue and transmits less heat to the surrounding contacted tissue.

In yet another embodiment, the heat-insulating coating 61 is formed by dispersively mixing, into a common resin material such as PEEK, two types of hollow particles (a first hollow particle and a second hollow particle) having different particle size distributions and each being heat-insulating. The first hollow particle is constituted of, for example, a glass (soda lime borosilicate glass) or silica (silicon dioxide) in the shape of a hollow spherical shell. The particle size of the first hollow particle is within a range of, for example, 20 to 30 μm. The second hollow particle is constituted of, for example, a glass (soda lime borosilicate glass) or silica (silicon dioxide) in the shape of a hollow cylinder with a bottom. The particle size of the second hollow particle is, for example, approximately 0.2 μm. Therefore, the shapes and particle size distributions of the two kinds of hollow particles are different from each other. Also, the volumetric distributions of the hollow portions of the two kinds of hollow particles, and the shapes of the hollow portions of the two kinds of hollow particles are different from each other.

In that case, the thermally transmitting path inside the heat-insulating coating 61 bypasses the aforementioned hollow particles. This makes the length of the thermally transmitting path longer than the actual thickness of the coating, and the heat-insulating coating 61 becomes less thermally transmitting. Also, the heat-insulating coating 61 includes multiple types of hollow particles in which the shapes of the hollow portions and the volumetric distributions are different from each other. This makes the composition of the heat-insulating coating 61 more complicated, and further lengthens the thermally transmitting path in the thickness direction of the heat-insulating coating 61. This further makes the heat-insulating coating 61 less thermally transmitting. Also, a hollow space (space filled with air) is formed inside each of the two types of hollow particles. In other words, all the hollow particles form a space inside the heat-insulating coating 61. Due to the heat-insulating effect of the hollow space formed inside, the heat-insulating coating 61 becomes less thermally transmitting.

The electrically conductive coating 62 is electrically conductive. In one embodiment, the electrically conductive coating 62 is formed by, for example, metal plating or the like.

In another embodiment, the electrically conductive coating 62 is formed from a mix of electrically conductive and electrically non-conductive materials. Examples for the electrically non-conductive material include fluorine-based resins such as PTFE (polytetrafluoroethylene) or PFA (perfluoroalkoxyalkane) and PAI (polyamideimide), PEEK (polyetheretherketone) and silica (silicon dioxide), or PEEK and aerosol. The electrically non-conductive material has at least one of the following additional functions: adhesion prevention of the living tissue, water repellency, oil repellency, abrasion resistance, thermal insulation, additive coloration, antihalation, etc. The electrically conductive material is, for example, copper, silver, gold etc., and preferably silver. In addition, the electrically conductive material is provided with a plurality of elements having different shapes. These elements are, for example, any of: flat or oblate, spherical, polyhedron-shaped, linear, and fiber-shaped. Also, the electrically conductive material may be solely composed of elements having the same shape.

In that case, the electrically conductive material is provided with a first and a second element having different shapes with respect to each other, thereby forming a cross-linking structure in the electrically conductive material of the electrically conductive coating 62. This keeps the electrostatic capacity great at the electrically conductive coating 62, and makes the electrically conductive coating 62 electrically conductive.

Figure 5:
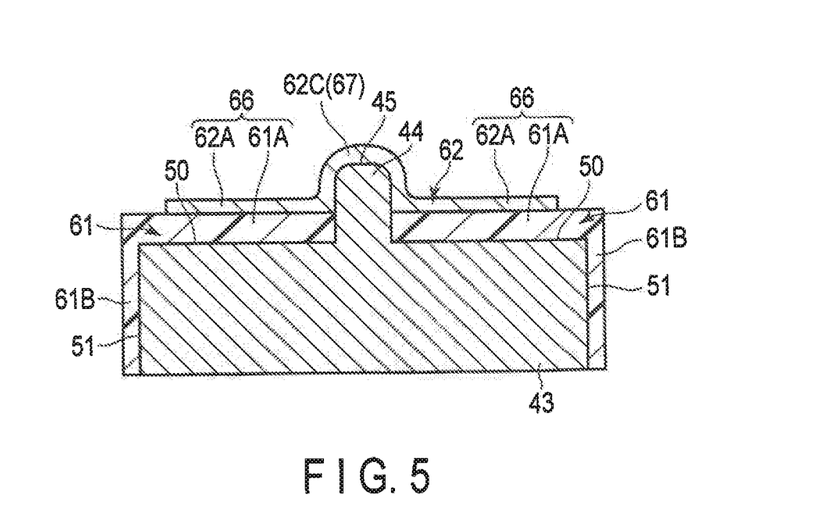
FIG. 5 is a cross-sectional view schematically showing the thermally transmitting member according to an exemplary embodiment in a cross section substantially perpendicular to the longitudinal axis.

FIG. 5 is a view showing the thermally transmitting member 43 of the first gripping piece 13 in a cross section substantially perpendicular to the longitudinal direction. As shown in FIG. 5, the heat-insulating coating 61 is formed continuously from the lateral surface 51 to the planar surface portion 50. The heat-insulating coating 61 has a first heat-insulating coating portion 61A provided on the planar surface portion 50, and a second heat-insulating coating portion 61B provided on the lateral surface 51. The first heat-insulating coating portion 61A is in close contact with the planar surface portion 50 from the side of the second gripping piece 14. The second heat-insulating coating portion 61B is in close contact with the lateral surface 51 from the outside in the width direction. The heat-insulating coating 61 is not provided on the protruding surface 45. The heat-insulating coating 61 is formed in the second gripping region F2 on the second opposing surface 16.

In the present embodiment, the electrically conductive coating 62 is continuously formed from the protruding surface 45 to the planar surface portion 50. The electrically conductive coating 62 has a first electrically conductive coating portion 62A provided on the planar surface portion 50 and a second electrically conductive coating portion 62C provided on the protruding surface 45. The first electrically conductive coating portion 62A is in close contact with the heat-insulating coating 61 from the side of the second gripping piece 14 in one part of the planar surface portion 50. The second electrically conductive coating portion 62C is in close contact with the protruding surface 45 from the side of the second gripping piece 14. The electrically conductive coating 62 is continuously formed in the first gripping region F1 and the second gripping region F2 on the first opposing surface 16.

In the planar surface portion 50, the first heat-insulating coating portion 61A is in close contact with the planar surface portion 50 from the side of the second gripping piece 14, and the first electrically conductive coating portion 62A is in close contact with one part of the first heat-insulating coating portion 61A from the side of the second gripping piece 14. In other words, on the planar surface portion 50, a laminated portion 66 is formed in which the electrically conductive coating 62 is laminated on the heat-insulating coating 61 from the outside (side of the second gripping piece 14). The laminated portion 66 is formed in the second gripping region F2 on the first opposing surface 16. Here, the planar surface portion 50 opposes the electrode surface 52 formed by the electrically conductive member 36 of the second gripping piece 14 (see FIG. 3). In other words, the laminated portion 66 is provided at a position opposed to the electrode (36) provided on the second gripping piece 14. In the laminated portion 66, the heat-insulating coating 61 is present between the planar surface portion 50 and the electrically conductive coating 62. Therefore, in the laminated portion 66, the thermally transmitting member 43 and the electrically conductive coating 62 are not in contact with each other.

Further, on the protruding surface 45, the second electrically conductive coating portion 62C is in close contact with the thermally transmitting member 43 from the side of the second gripping piece 14. In other words, on the protruding surface 45, a single layer portion 67 is formed in which the electrically conductive coating 62 is in close contact with the opposing surface (45) of the base (43) from the outside (side of the second gripping piece 14). The single layer portion 67 is formed continuously with the laminated portion 66. In other words, between the single layer portion 67 and the laminated portion 66, the electrically conductive coating 62 is continuously extended. Further, the single layer portion 67 is formed on the first opposing surface 16 in the first gripping region F1. In the single layer portion 67, the second electrically conductive coating portion 62C is in contact with the thermally transmitting member 43 via the protruding surface 45. Therefore, the electrically conductive coating 62 is electrically connected to the thermally transmitting member 43.

Next, the actions and effects of the energy treatment instrument 1 being the medical device of the present embodiment will be described. For performing treatment using the energy treatment instrument 1, the surgeon holds the housing 4 of the energy treatment instrument 1 and inserts the end effector 6 into a cavity of the body such as an abdominal cavity or the like. The object to be treated, such as a blood vessel, is placed between the gripping pieces 13, 14, and the handle 12 is closed with respect to the grip 11, thereby closing the gripping pieces 13, 14. As a result, the blood vessel is gripped between the gripping pieces 13, 14.

Figure 6:
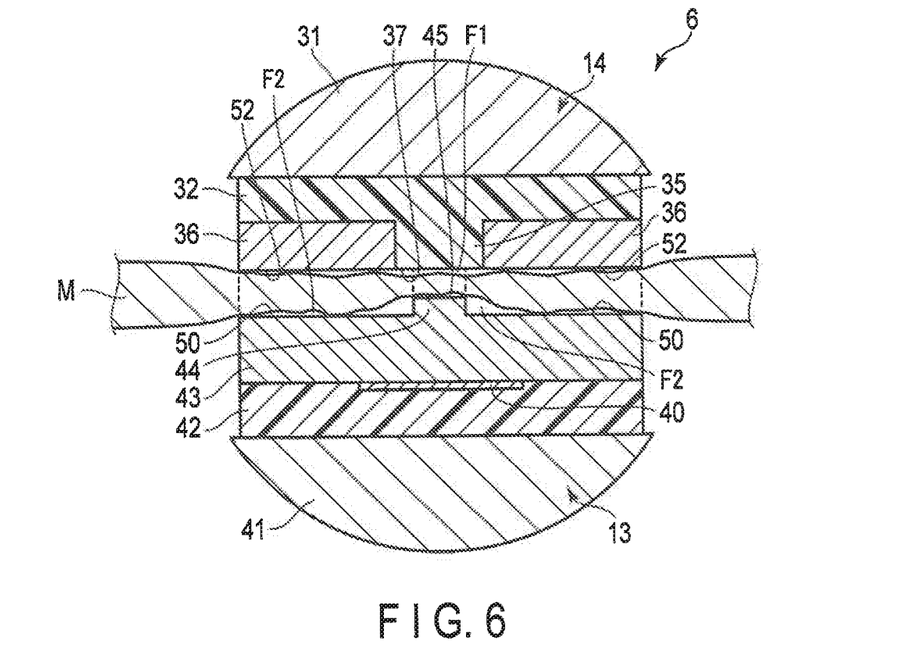
FIG. 6 is a cross-sectional view schematically showing a state in which a living tissue is gripped by the end effector according to an exemplary embodiment in a cross section substantially perpendicular to the longitudinal axis.

FIG. 6 is a view showing a state in which a living tissue M is gripped between the gripping pieces 13, 14. In this state, by operating the energy operation input unit (operation button 19), electric energy (high frequency electric power) is supplied from the second energy output supply 9 to each of: the thermally transmitting member 43 and the electrically conductive member 36. Supplying electric energy to each of: the thermally transmitting member 43 and the electrically conductive member 36 allows a high-frequency current to flow through the gripped living tissue M between the first opposing surface 16 and the electrode surface 52 of the second opposing surface 17. In this way, the living tissue M is coagulated in the first gripping region F1 and in the second gripping region F2.

Also, by operating the energy operation input unit (operation button 19), electric energy is supplied from the first energy output supply 8 to the thermal source 40. The electric energy supplied to the thermal source 40 generates heat in the thermal source 40. The heat generated in the thermal source 40 is applied to the living tissue M via the thermally transmitting member 43 and the protruding surface 45. In other words, the heat is applied to the living tissue M in the first gripping region F1.

Further, the distance between the first opposing surface 16 and the second opposing surface 17 in the first gripping region F1 is smaller than the distance between the first opposing surface 16 and the second opposing surface 17 in the second gripping region F2. Therefore, the amount of gripping force applied to the living tissue M gripped in the first gripping region F1 is larger than the amount of gripping force applied to the living tissue M gripped in the second gripping region F2.

In the first gripping region F1, heat is applied to the living tissue M and a comparatively large amount of gripping force is applied to the gripped living tissue M. By properly applying heat and the amount of gripping force to the living tissue M, the living tissue M is incised in the first gripping region F1. In other words, the first gripping region F1 functions as an incision portion for incising the gripped living tissue.

In the present embodiment, the laminated portion 66 is formed on the planar surface portion 50. In the laminated portion 66, the thermally transmitting member 43 and the first electrically conductive coating portion 62A are not in contact with each other. Therefore, heat from the thermal source 40 is hardly transmitted from the planar surface portion 50 to the first electrically conductive coating portion 62A. Also, the heat from the thermal source 40 is transmitted to the first electrically conductive coating portion 62A via a thermal path running through the protruding surface 45 and the second electrically conductive coating portion 62C. Since this thermal path is relatively long, the heat is not easily transmitted to the first electrically conductive coating portion 62A. Therefore, intense thermal transmission from the thermal source 40 to the electrically conductive coating 62 only occurs at the protruding surface 45. In other words, the portion on the first opposing surface 16 with intense thermal transmission is limited to the first gripping region F1. Since the portion on the first opposing surface 16 with intense thermal transmission is limited to the first gripping region F1, heat is prevented from being conducted to portions of the living tissue M located outside the gripping regions F1, F2. In other words, heat invasion to any living tissue or the like other than the object to be treated is reduced.

Further, the electrically conductive coating 62 is electrically connected to the thermally transmitting member 43. Therefore, electric energy supplied to the thermally transmitting member 43 is transmitted to the first electrically conductive coating portion 62A of the laminated portion 66. Here, the laminated portion 66 is formed at a position opposing the second electrode (36). Therefore, by supplying electric energy to the first electrically conductive coating portion 62A, the current density of the high-frequency current flowing in the living tissue M increases between the second electrode (36) and the first electrically conductive coating portion 62 that is the first electrode. Also, the high-frequency current flows through the living tissue M even between the second electrode (36) and the second electrically conductive coating portion 62C. Therefore, the high-frequency current is properly applied to the gripped living tissue M between the second electrode (36) and the electrically conductive coating 62. By forming the heat-insulating coating 61 and the electrically conductive coating 62 as described above, heat invasion to any living tissue or the like other than the object to be treated is reduced, and high-frequency current to the object to be treated is applied properly.

During treatment of a living tissue, the living tissue may, in some cases, come into contact with the lateral surface 51 from the outside in the width direction of the end effector 6. In the present embodiment, the heat-insulating coating 61 is provided with the second heat-insulating coating portion 61B formed on the lateral surface 51. Therefore, even when the living tissue comes into contact with the lateral surface 51, heat application to the portion in contact with the lateral surface 51 in the living tissue is suppressed. In addition, the high-frequency current is prevented from being applied to the portion of the living tissue contacting the lateral surface 51 via the lateral surface 51 of the thermally transmitting member 43. This effectively prevents the high-frequency current from being applied to portions other than the living tissue portion to be coagulated. It should be noted that in a modification, the heat-insulating coating 61 may not be formed on the lateral surface 51.

Figure 7:
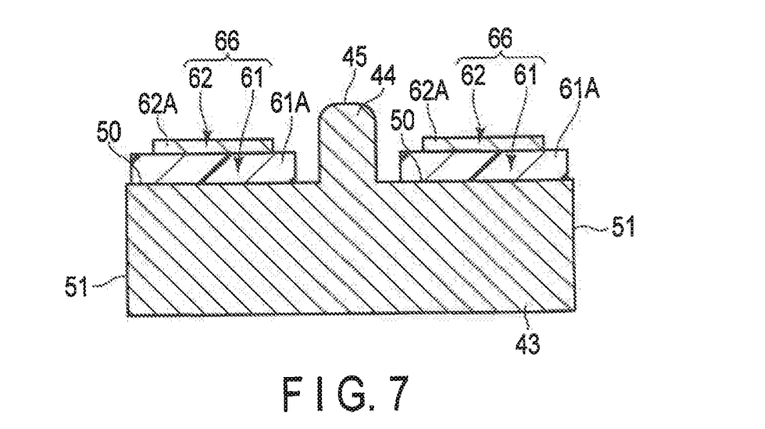
FIG. 7 is a cross-sectional view schematically showing a thermally transmitting member according to an exemplary embodiment in a cross section substantially perpendicular to the longitudinal axis.

The single layer portion 67 may not be provided. FIG. 7 is a view showing the thermally transmitting member 43 in a cross section substantially perpendicular to the longitudinal direction. As shown in FIG. 7, the heat-insulating coating 61 is provided solely on the planar surface portion 50. In other words, the heat-insulating coating 61 only has the first heat-insulating coating portion 61A that is provided on the planar surface portion 50, and the heat-insulating coating 61 is only formed in the second holding area F2. The heat-insulating coating 61 is in close contact with the planar surface portion 50 from the side of the second gripping piece 14.

The electrically conductive coating 62 is provided solely in the planar surface portion 50. In this planar surface portion 50, the electrically conductive coating 62 is in close contact with one part on the first heat-insulating coating portion 61A from the side of the second gripping piece 14. In other words, the electrically conductive coating 62 only has the first electrically conductive coating portion 62A provided in the planar surface portion 50 and the electrically conductive coating 62 is formed only in the second holding area F2.

Formed in this modification as well is, on the planar surface portion 50, the laminated portion 66 in which the electrically conductive coating 62 is laminated on the heat-insulating coating 61 from the outside (side of the second gripping piece 14). Also, the laminated portion 66 is formed in the second gripping region F2 on the first opposing surface 16, and is provided at a position opposed to the electrode (36) provided at the second gripping piece 14.

In the present modification, one end of an electric path (not shown) is connected to the electrically conductive coating 62. The electric path extends through the interior of the shaft 5, inside the housing 4, and inside the cable 7, and it is electrically connected to the second energy output supply 9 of the power supply unit 3. The electrically conductive coating 62 functions as a (first) electrode by supplying electrical energy (high frequency electric power) from the second energy output supply 9.

In the present modification, electric energy from the second energy output supply 9 is not supplied to the thermally transmitting member 43 that is the base. Therefore, the thermally transmitting member 43 may be formed from an electrically non-conductive material such as, for example, aluminum nitride.

In the present modification as well, the laminated portion 66 is formed on the planar surface portion 50. In this way, heat from the thermal source 40 is hardly transmitted from the planar surface portion 50 to the first electrically conductive coating portion 62A. Therefore, the portion on the first opposing surface 16 with intense thermal transmission can be limited to the first gripping region F1, and heat invasion to any living tissue or the like other than the object to be treated is reduced. In other words, heat invasion to the outside of the gripping regions F1, F2 is reduced.

In the present modification, electric energy is directly supplied via the aforementioned electric path to the first electrically conductive coating portion 62A. Therefore, in the present modification as well, the first electrically conductive coating portion 62A functions as the first electrode opposed to the second electrode (36). Supplying electric energy to the first electrically conductive coating portion 62A increases the current density of the high-frequency current flowing to the living tissue between the second electrode (36) and the first electrically conductive coating portion 62A that is the first electrode, and allows high-frequency current to be properly applied to the gripped living tissue. Therefore, in the present modification as well, heat invasion to portions located on the outside of the gripping region of the living tissue is suppressed, and high-frequency current to the living tissue is applied properly.

Figure 8:
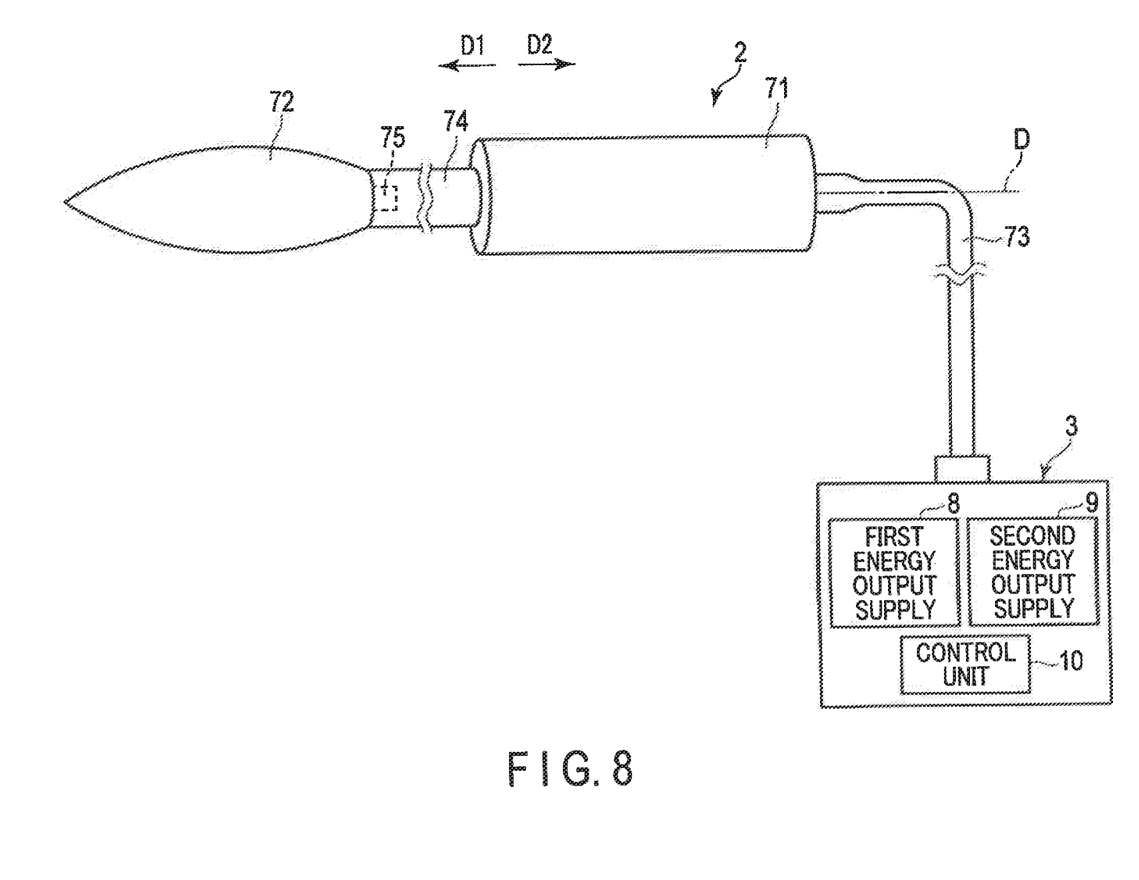
FIG. 8 is a schematic view showing the treatment system using an energy treatment instrument according to an exemplary embodiment.

The configuration of the end effector 6 is not limited to what is described above. As an example, the protruding portion 44 may not be provided on the first gripping piece 13 on which the thermal source 40 is provided. In that case, a protruding portion protruding from the second opposing surface 17 towards the first gripping piece 13 is formed on the second gripping piece 14. When the gripping pieces 13, 14 are closed, the protruding portion abuts against the first opposing surface 16. The first gripping region F1 is formed between the protruding portion and the portion on the first opposing surface 16 where the protruding portion is abutting. In the first gripping region F1, the first opposing surface 16 is pressed by the protruding portion to the side of the first gripping piece 13. In this way, the force with which the first gripping piece 13 presses the second gripping piece 14 in the first gripping region F1 is greater than the force with which the first gripping piece 13 presses the second gripping piece 14 in the second gripping region F2 outside the first gripping region F1. FIG. 8 is a view showing a treatment system in which an energy treatment instrument 2 is used. As shown in FIG. 8, the energy treatment instrument 2 has a longitudinal axis D. Here, in the energy treatment instrument 2, the direction along the longitudinal axis D will be referred to as the longitudinal direction. Also, one side in the longitudinal direction will be referred to as the distal side (arrow D1 side), while the side opposing the distal side will be referred to as the proximal side (arrow D2 side). In the present embodiment as well, the energy treatment instrument 2 is a thermal treatment tool for treating an object to be treated such as a living tissue by using heat as energy. Further, in the present embodiment, the energy treatment instrument 2 is provided with a treatment electrode, and is configured as a monopolar high-frequency treatment tool for treating an object to be treated by using high-frequency energy (high-frequency current) flowing between the treatment electrode and a return electrode attached to the human body.

The energy treatment instrument 2 is provided with a housing 71 capable of holding, a shaft 74 connected to the distal side of the housing 71, and a plate-shaped blade 72 (base) provided in the distal portion of the shaft 74. Connected to the housing 71 is one end of a cable 73. The other end of the cable 73 is separably connected to the aforementioned power supply unit 3.

Attached to the housing 71 is the operation button (not shown) as the energy operation input unit. By pressing the operation button, the power supply unit 3 is operated (a signal is input to the power supply unit 3) to output electric energy from the first energy output supply 8 and/or the second energy output supply 9 to the energy treatment instrument 2. It should be noted that instead of or in addition to the operation button, a foot switch or the like separate from the energy treatment instrument 2 may be provided as the energy operation input unit.

The blade 72 extends along the longitudinal axis D. The blade 72 is formed from an electrically conductive, highly thermally transmitting material. The blade 72 is formed from, for example, metal or the like. The blade 72 is electrically connected to the second energy output supply 9 of the power supply unit 3 via an electric path (not shown) extending through the inside of the housing 71 and the inside of the cable 73. By supplying electric energy (high frequency electric power) from the second energy output supply 9, the blade 72 functions as the treatment electrode of the monopolar high-frequency treatment tool.

Provided inside the shaft 74 is a thermal source 75. The thermal source 75 is electrically connected to the first energy output supply 8 of the power supply unit 3 via the electric path (not shown) extending through the inside of the housing 71 and the inside of the cable 73. In the thermal source 75, heat is generated by supplying electric energy from the first energy output supply 8. The thermal source 75 is in contact with the blade 72. In this way, heat generated by the thermal source 75 is transmitted to the blade 72. It should be noted that the thermal source 75 may be provided inside the blade 72.

Figure 9:
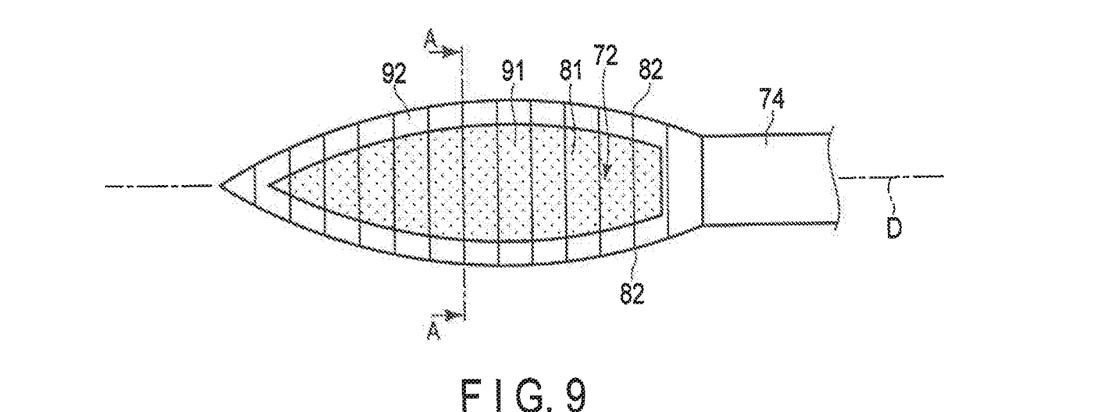
FIG. 9 is a schematic view showing a shaft and a blade according to an exemplary embodiment as viewed from one side in the width direction.
Figure 10:
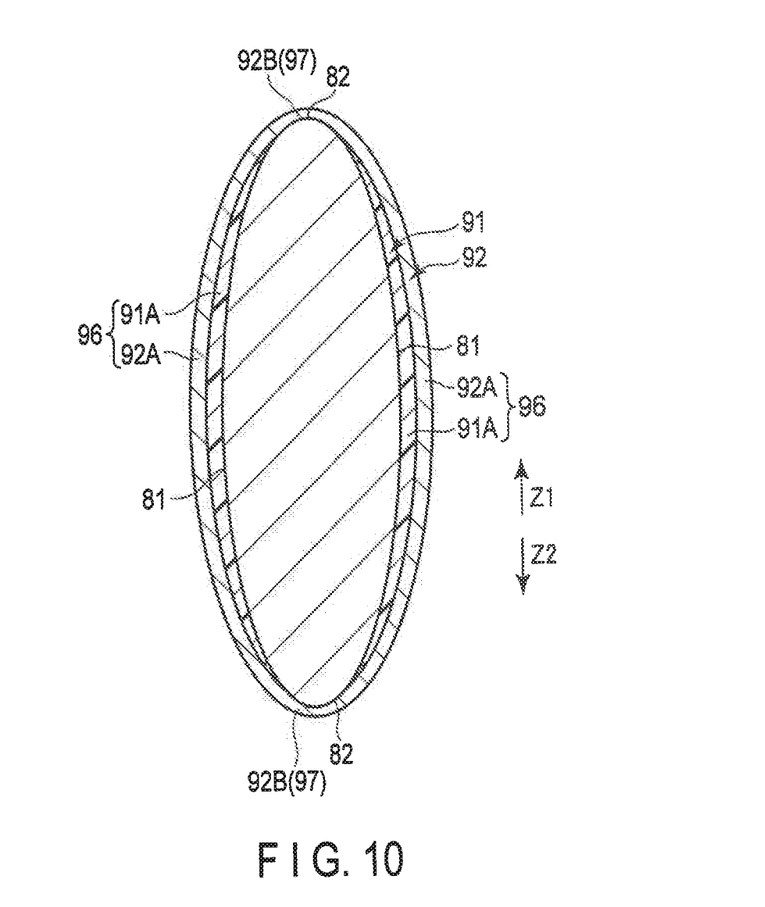
FIG. 10 is a cross-sectional view schematically showing a cross section taken along a line A-A shown in FIG. 9.

FIG. 9 is a view showing the shaft 74 and the blade 72. FIG. 10 is a cross-sectional view along the line A-A shown in FIG. 9. FIG. 10 is a view showing the blade 72 in a cross section substantially perpendicular to the longitudinal axis D. As shown in FIGS. 9 and 10, the blade 72 is provided with a lateral surface 81 facing in a direction substantially perpendicular to the longitudinal axis D, and edge portions 82 forming the edge of the blade 72. Here, the direction in which the lateral surface 81 is facing will be referred to as the width direction of the blade 72. Likewise, the (substantially perpendicular) direction intersecting the longitudinal axis D and the width direction will be referred to as the perpendicular direction. In the perpendicular direction, one side will be referred to as the upper side (arrow Z1 in FIG. 10), while the side opposing the upper side will be referred to as the lower side (arrow Z2 in FIG. 10). One of the edge portions 82 becomes sharper towards the upper side, while the other cutting portion becomes sharper towards the lower side.

Coated on one part of the outer surface of the blade 72 is a heat-insulating coating 91 (first coating). In FIG. 9, the heat-insulating coating 91 is indicated by the dotted hatching. The heat-insulating coating 91 is formed from an electrically non-conductive material, less thermally transmitting than the blade 72. The heat-insulating coating 91 is formed from the same material as the heat-insulating coating 61. Coated on one part of the outer surface of the blade 72 is an electrically conductive coating 92 (second coating). In FIG. 9, the electrically conductive coating 92 is indicated by the hatching with the vertical lines. The electrically conductive coating 92 is electrically conductive. The electrically conductive coating 92 is formed from the same material as the electrically conductive coating 62.

The heat-insulating coating 91 can have a first heat-insulating coating portion 91A provided on the lateral surface 81. The first heat-insulating coating portion 91A is in close contact with the lateral surface 81 from the outside in the width direction of the blade 72. The heat-insulating coating 91 is not provided in the edge portions 82. The electrically conductive coating 92 is formed continuously with the lateral surface 81 and the edge portions 82. The electrically conductive coating 92 has a first electrically conductive coating portion 92A provided on the lateral surface 81, and a second electrically conductive coating portion 92B provided in the edge portions 82. The first electrically conductive coating portion 92A is in close contact on the lateral surface 81 with one part of the heat-insulating coating 91 from the outside in the width direction. The second electrically conductive coating portion 92B is in close contact with the edge portions 82 from the upper or lower side. The electrically conductive coating 92 is exposed to the outside on the outer surface of the blade 72.

On the lateral surface 81, the first heat-insulating coating portion 91A is in close contact with the lateral surface 81 from the outside in the width direction. The first electrically conductive coating portion 92A is in close contact with one part on the first heat-insulating coating portion 91A from the outside in the width direction. In other words, formed on the lateral surface 81 is a laminated portion 96 in which the electrically conductive coating 92 is laminated on the heat-insulating coating 91 from the outside. In the laminated portion 96, the heat-insulating coating 91 is present between the lateral surface 81 and the electrically conductive coating 92. Therefore, in the laminated portion 96, the blade 72 and the electrically conductive coating 92 are not in contact.

Further, in the edge portions 82, the second electrically conductive coating portion 92B is in close contact with the blade 72 from the upper or lower side. In other words, formed in the edge portions 82 are a single layer portion 97 in which the electrically conductive coating 92 is in close contact with the outer surface (82) of the base (72) from the upper or lower side. The single layer portion 97 is formed continuously with the laminated portion 96. In other words, the electrically conductive coating 92 is continuously extends between the single layer portion 97 and the laminated portion 96. In the single layer portion 97, the second electrically conductive coating portion 92B is in contact with the blade 72 via the edge portions 82. In this way, the electrically conductive coating 92 is electrically connected to the blade 72.

Next, the actions and effects of the energy treatment instrument 2 being the medical device of the present embodiment will be described. For performing treatment using the energy treatment instrument 2, a return electrode is attached to the patient. The surgeon then holds the housing 71 of the energy treatment instrument 2 and operates the energy operation input unit. By operating the energy operation input unit (operation button 19), electric energy is supplied from the second energy output supply 9 to the blade 72. In other words, the treatment electrode is formed on the edge portions 82 and the lateral surface 81. Also, by operating the energy operation input unit, electric energy is supplied from the first energy output supply 8 to the thermal source 75. Supplying electric energy to the thermal source 75 generates heat in the thermal source 75, and the generated heat is transmitted to the blade 72.

When incising the object to be treated such as a living tissue by using the energy treatment instrument 2, the surgeon presses the edge portions 82 of the blade 72 against the living tissue while electric energy (high frequency electric power) and heat are being supplied to the blade 72. High-frequency current flows through the living tissue and the body between the cutting portion 82 and the return electrode. In other words, heat and high-frequency current are applied to the living tissue. Further, the living tissue is pressed in the edge portions 82. In this way, high-frequency current, heat, and pressing force are applied to the living tissue in the edge portions 82. In this manner, the living tissue is coagulated and incised. In other words, the edge portions 82 are incision portions for incising the living tissue.

In the present embodiment, formed on the lateral surface 81 is the laminated portion 96. In this laminated portion 96, the blade 72 and the first electrically conductive coating portion 92A are not in contact with each other. Therefore, heat from the thermal source 75 is hardly transmitted from the lateral surface 81 to the first electrically conductive coating portion 92A. Also, heat from the thermal source 75 is transmitted to the first electrically conductive coating portion 92A via a thermal path extending through the edge portions 82 and the second electrically conductive coating portion 92B. Since this thermal path is relatively long, heat is not easily transmitted to the first electrically conductive coating portion 92A. In this way, intense thermal transmission from the thermal source 75 to the electrically conductive coating 92 only occurs in the edge portions 82. In other words, the section on the outer surface of the blade 72 with intense thermal transmission is limited to the incision portions (edge portions 82). By limiting the section with intense thermal transmission to the incision portions in the outer surface of the blade 72, heat invasion to any living tissue or the like other than the object to be treated is reduced.

For coagulating the object to be treated such as a living tissue by using the energy treatment instrument 2, the surgeon presses the lateral surface 81 of the blade 72 against the living tissue while high frequency electric power and heat are being supplied to the blade 72. Through the living tissue and the inside of the body, high-frequency current flows between the lateral surface 81 and the return electrode. In other words, high-frequency current is applied to the living tissue. On the lateral surface 81, applying only high-frequency current to the living tissue coagulates the living tissue. In other words, by selecting properly the portions to be brought into contact with the object to be treated, the surgeon can select the treatment method properly.

In the edge portions 82, the electrically conductive coating 92 is electrically connected to the blade 72. Therefore, the electric energy supplied to the blade 72 is transmitted to the first electrically conductive coating portion 92A of the laminated portion 96. By supplying electric energy to the first electrically conductive coating portion 92A, high-frequency current properly flows to the living tissue between the return electrode and the first electrically conductive coating portion 92A being the treatment electrode. In this way, high-frequency current is properly applied to the living tissue via the first electrically conductive coating 92A. By forming the heat-insulating coating 91 and the electrically conductive coating 92 as described above, heat invasion to the living tissue or the like other than the portion to be treated is reduced, and high-frequency current to the living tissue is applied properly.

It should be noted that the single layer portion 97 may not be provided. In that case, the electrically conductive coating 92 is provided only on the lateral surface 81, and on the lateral surface 81, the electrically conductive coating 92 is laminated on the first heat-insulating coating portion 91A from the outside in width direction. Also, the electrically conductive coating 92 is electrically connected to the second energy output supply 9 of the power supply unit 3 via an electric path (not shown) extending through the inside of the shaft 74, the inside the housing 71, and the inside the cable 7. By supplying electric energy (high-frequency energy) from the second energy output supply 9, the electrically conductive coating 62 functions as the treatment electrode. In the present modification, the electric energy from the second energy output supply 9 is not supplied to the blade 72 that is the base. As a result, the blade 72 may be formed from an electrically non-conductive material such as, for example, aluminum nitride.

It should be noted that the configuration described in the aforementioned embodiments etc. can also be applied to various medical devices that supply heat and electric energy to contacted living tissue.

In the aforementioned embodiments etc., the medical device (1; 2) is provided with: the thermal source (40; 74) that generates heat; the base (43; 72) that has the outer surface (45, 50, 51; 81, 82) and to which the heat from the thermal source (40; 74) is transmitted; the first coating (61; 91) that is in close contact with one part of the outer surface of the base (43; 72) from the outside and that is less thermally transmitting than the base (43; 72); the second coating (62; 92) that is: provided on the outer surface (45, 50, 51; 81, 82) of the base (43; 72), exposed to the outside, electrically conductive, and supplies, as electrical energy is supplied, a high-frequency current to the object to be treated; and the laminated portion (66; 96) that is provided in at least one part of a site in which the first coating (61; 91) in the outer surface (45, 50, 51; 81, 82) of the base (43; 72) extends, and in which the second coating (62; 92) is laminated on the first coating (61; 91) from the outside.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device, comprising:
a thermal source that generates heat;
a base that has an outer surface configured to receive the heat generated from the thermal source;
a first coating that contacts one part of the outer surface of the base and that is less thermally transmitting than the base;
a second coating that contacts the first coating and the outer surface of the base, the second coating being exposed and electrically conductive, and configured to conduct a high-frequency current supplied to the base to an object to be treated;
a laminated portion that includes the first coating that extends along the outer surface of the base, and a portion of the second coating that is laminated on the first coating;
a single layer portion extending along a centerline of the base and contacting the outer surface of the base, the single layer portion being formed of the second coating, wherein:
the first coating is thicker than the second coating;
in the single layer portion, the second coating contacts the base from an outside;
in the laminated portion, the first coating contacts the base from the outside such that the first coating is provided between the base and the second coating;
the single layer portion includes a protrusion that protrudes beyond a top surface of the first coating; and
the single layer portion is provided on top of the protrusion; and
a jaw that is configured to open and close with respect to the base and that is configured to grip the object to be treated between the jaw and the base, wherein:
the outer surface of the base is an opposing surface opposing the jaw,
the laminated portion is provided on the opposing surface,
the opposing surface includes a first portion and a second portion configured to press the jaw with less force than the first portion, and
the laminated portion is provided in the second portion.

2. The medical device according to claim 1, wherein
the base is electrically conductive,
the single layer portion directly contacts the outer surface of the base, and
the second coating extends continuously between the single layer portion and the laminated portion.

3. The medical device according to claim 2, further comprising a power supply configured to supply electrical energy to the second coating via the base in the single layer portion.

4. The medical device according to claim 1, wherein
the base is electrically non-conductive,
the single layer portion directly contacts the outer surface of the base from the outside,
an electric path configured to transmit electric energy is connected to the second coating, and
the second coating extends continuously between the single layer portion and the laminated portion.

5. The medical device according to claim 1, wherein
the base is electrically conductive,
the single layer portion directly contacts the opposing surface of the base, and
the second coating extends continuously between the single layer portion and the laminated portion.

6. The medical device according to claim 1, wherein
the jaw includes an electrode, and
the laminated portion is provided at a position opposing the electrode.

7. The medical device according to claim 1, wherein the first coating is formed from a heat resistant resin.

8. The medical device according to claim 1, wherein the first coating is formed from a mix in which hollow particles are mixed in a resin material.

9. The medical device according to claim 1, wherein the second coating is formed from a mixture of an electrically non-conductive material and an electrically conductive material, the mixture being electrically conductive.

10. The medical device according to claim 9, wherein the electrically conductive material is silver.

11. The medical device according to claim 9, wherein the electrically non-conductive material is fluororesin.

12. The medical device according to claim 1, wherein the thermal source is a heater.

13. A medical device, comprising:
a thermal source that generates heat by supplying electric energy to the thermal source;
a base that extends in a longitudinal direction and includes an outer surface, and the base is configured to receive the heat generated by the thermal source;
a first coating that contacts one part of the outer surface of the base and that is less thermally transmitting than the base;
a second coating that contacts the first coating and the outer surface of the base such that one part of the second coating is laminated on the first coating;
a laminated portion that includes the first coating that extends along the outer surface of the base, and a portion of the second coating that is laminated on the first coating; and
a single layer portion extending along a centerline of the base and contacting the outer surface of the base, the single layer portion being formed of the second coating, wherein:
the first coating is thicker than the second coating;
in the single layer portion, the second coating contacts the base from an outside;
in the laminated portion, the first coating contacts the base from the outside such that the first coating is provided between the base and the second coating;
the single layer portion includes a protrusion that protrudes beyond a top surface of the first coating; and
the single layer portion is provided on top of the protrusion.

* * * * *